US008187255B2

(12) United States Patent
Weber et al.

(10) Patent No.: US 8,187,255 B2
(45) Date of Patent: May 29, 2012

(54) MEDICAL DEVICES HAVING NANOPOROUS COATINGS FOR CONTROLLED THERAPEUTIC AGENT DELIVERY

(75) Inventors: Jan Weber, Maastricht (NL); Liliana Atanasoska, Edina, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1518 days.

(21) Appl. No.: 11/701,768

(22) Filed: Feb. 2, 2007

(65) Prior Publication Data

US 2008/0188836 A1   Aug. 7, 2008

(51) Int. Cl.
*A61K 9/22* (2006.01)
*A61F 2/06* (2006.01)
*G01N 21/75* (2006.01)
*G01N 31/22* (2006.01)
*G01N 33/52* (2006.01)

(52) U.S. Cl. .................. 604/890.1; 623/1.39; 623/1.42; 424/424

(58) Field of Classification Search .................. 604/264, 604/93.01, 890.1–892.1, 19; 623/1.15, 1.42, 623/1.39; 424/423–426
See application file for complete search history.

(56) References Cited

U.S. PATENT DOCUMENTS

| 5,733,925 | A | 3/1998 | Kunz et al. ............ 514/449 |
| 6,156,435 | A | 12/2000 | Gleason et al. ........ 428/422 |
| 6,399,528 | B1 | 6/2002 | Krell et al. ........... 501/80 |
| 6,517,888 | B1 | 2/2003 | Weber .................. 427/2.24 |
| 6,583,048 | B1 | 6/2003 | Vincent et al. ......... 438/623 |
| 6,887,578 | B2 | 5/2005 | Gleason et al. ........ 428/447 |
| 2003/0064095 | A1 | 4/2003 | Martin et al. .......... 424/451 |
| 2004/0148015 | A1 | 7/2004 | Lye et al. ............. 623/1.15 |
| 2005/0050859 | A1* | 3/2005 | Coppeta et al. .......... 53/471 |
| 2005/0070989 | A1 | 3/2005 | Lye et al. .............. 623/1.4 |
| 2005/0118229 | A1 | 6/2005 | Boiarski ............... 424/424 |
| 2005/0208100 | A1 | 9/2005 | Weber et al. .......... 424/426 |
| 2006/0127442 | A1 | 6/2006 | Helmus et al. ......... 424/423 |

(Continued)

FOREIGN PATENT DOCUMENTS

EP   1891995 A   2/2008
(Continued)

OTHER PUBLICATIONS

Tejal A. Desai et al., "Characterizatoin of Micromachined Silicon Membranes for Immunoisolation and bioseparation Applications", *J. Membrane Science*, 159, 1999, pp. 221-231.

(Continued)

*Primary Examiner* — Matthew F Desanto
(74) *Attorney, Agent, or Firm* — Mayer & Williams PC; David B. Bonham; Keum J. Park (57) ABSTRACT

According to an aspect of the invention, medical devices are provided which include a substrate, at least one porous reservoir containing at least one therapeutic agent disposed over the substrate, at least one nanoporous layer disposed over the at least one porous reservoir, and at least one plugged aperture, which may be located within the substrate, within the nanoporous layer, or both. According to another aspect of the invention, a method of forming a medical device is provided which includes (a) forming a porous reservoir over a substrate, (b) forming a nanoporous layer over the porous reservoir, (c) forming an aperture within the substrate or the nanoporous layer, (d) filling the porous reservoir with therapeutic agent through the aperture, and (d) plugging the aperture.

39 Claims, 3 Drawing Sheets

U.S. PATENT DOCUMENTS

| | | | |
|---|---|---|---|
| 2006/0127443 A1 | 6/2006 | Helmus et al. | 424/423 |
| 2006/0129215 A1 | 6/2006 | Helmus et al. | 607/115 |
| 2006/0171985 A1 | 8/2006 | Richard et al. | 424/423 |
| 2008/0086113 A1 | 4/2008 | Tenney et al. | |

FOREIGN PATENT DOCUMENTS

| | | | |
|---|---|---|---|
| WO | | 2006063157 A | 6/2006 |

OTHER PUBLICATIONS

H. Wieneke et al., "Synergistic Effects of a Novel Nanoporous Stent Coating and Tacrolimus on Intima Proliferation in Rabbits", *Catheterization and Cardiovascular Interventions*, 2003, vol. 60, 3, pp. 399-407.

Erin E. Leary Swan et al., "Fabrication and evaluation of nanoporous alumina membranes for osteoblast culture", *Journal of Biomedical Materials Research Part A*, vol. 72A, Issue 3, pp. 288-295, Published Online: Jan. 14, 2005.

Gi-Ra Yi et al., "Ordered Macroporous Particles by Colloidal Templating", *Chem. Mater.*, 2001, 13, pp. 2613-2618.

R. Suresh Singh et al., "Fabrication of nanoporous $TiO_2$ films through Benard-Marangoni convection", *Materials Resources Innovations*, Aug. 18, 2001, 2002, 5, pp. 178-184.

F. Martin et al., "Tailoring width of microfabricated nanochannels to solute size can be used to control diffusion kinetics", *Journal of Controlled Release*, 102, 2005, pp. 123-133.

L. Leoni et al., "Nanoporous Platforms for Cellular Sensing and Delivery", *Sensors*, 2002 2, pp. 111-120.

J. Erlebacher et al., "Evolution of nanoporosity in de-alloying", *Nature*, vol. 410, Mar. 22, 2001, pp. 450-453.

A.J. Forty, "Corrosion micromorphology of noble metal alloys and depletion gilding", *Nature*, vol. 282, Dec. 6, 1979, pp. 597-598.

R.C. Newman et al., "Alloy Corrosion", *MRS Bulletin*, Jul. 1999, pp. 24-28.

H.X. He et al., "Electrochemical fabrication of metal nanowires"in *Encyclopedia of Nanoscience and Nanotechnology*, Eds., N.S. Nalwa. American Scientific Publisher, 2003.

J. A. Paik et al., "Micromachining of mesoporous oxide films for microelectromechanical system structures", *J. Mater. Res.*, vol. 17, No. 8, Aug. 2002, p. 2121-2129.

Vanessa .Z -.H. Chan et al., "Ordered Bicontinuous Nanoporous and Nanorelief Ceramic Films from Self Assembling Polymer Precursors", *Science*, Nov. 26, 1999: vol. 286, No. 5445, pp. 1716-1719.

Sun J. et al., "Synthesis of Hierarchically Structured Nanoporous Materials with a Controlled Bimodal Pore Size Distribution", presentation at Nanoscale Science and Engineering Topical Conference, Nov. 2001. https://engineering.purdue.edu.ChE/Nano/NanoChmE.NSE__Topical__2001/SynthesisandCharacterizationofNovelNanoporousMaterials2.htm.

L. Vaccari et al., "Porous silicon as drug carrier for controlled delivery of doxorubicin anticancer agent", *Microelectronic Engineering*, 83, 2006, pp. 1598-1601.

Lippert T. et al., "Chemical and Spectroscopix Aspects of Polymer Ablation: Special Features and Novel Directions", *Chem. Rev.*, 103, 2, pp. 453-485, Feb. 2003.

Meijer J. et al., "Laser Machining by short and ultrashort pulses, state of the art and new opportunities in the age of photons", *Annals of the CIRP*, 51, 2, pp. 531-550, 2002.

J. Bekesi et al., "Efficient submicron processing of metals with femtosecond UV pulses", *Appl. Phys. A.*, 76, pp. 355-357, 2003.

D. Shamiryan et al., "Comparative study of SiOCH low-k films with varied porosity interacting with etching and cleaning plasma", *J. Vac. Sci .Technol. B.*, 20, 5, Sep./Oct. 2002, pp. 1923-1928.

K.K. S. Lau et al., "Hot-wire chemical vapor deposition (HWCVD) of fluorocarbon and organosilicon thin films", *Thin Solid Films*, 395, 2001, pp. 288-291.

C.S. Montross et al., "Laser shock processing and its effects on microstructure and properties of metal alloys: a revue", *International Journal of fatigue*, 24, 2002, pp. 1021-1036.

M. C. Gohel et al., "Modulation of active pharmaceutical material release from a novel 'tablet in capsule system' containing an effervescent blend", *Journal of Controlled Release*, 79, 2002, pp. 157-164.

Rita D'Aquino, "Good Drug Therapy: It's Not Just the Molecule—It's the Delivery", www.cepmagazin.org., Feb. 2004 CEP.

G. Orive et al., "Techniques: New approaches to the delivery of biopharmaceuticals", *Trends in Pharmacological Sciences*, vol. 25, No. 7, Jul. 2004, pp. 382-387.

http://www.hmi.de/people/chemseddine/group.htm, downloaded Sep. 13, 2006.

http://www.rpi.edu/locker/25/001225/public__html/nano__02/cregan/regan/mesoporous.html.

http://www.ccmr.cornell.edu/~uli/Pages/mesoporous.html, Weisner Research Group, Mesoporous Materials /through Self-Esteem, 1-2 date unknown but before the filing of this application.

http://web.mit.edu/newsoffice/nr/1999/gyroid.html, MIT researchers intricate ceramic nanostructures have many potential uses, MIT News, 1-3, Nov. 25, 1999.

https://engineering.purdue.edu.ChE/Nano/NanoChmE.NSE__Topical__2001/SynthesisandCharacterizationofNovelNanoporousMaterials2.htm, 2001, pp. 1-8.

\* cited by examiner

Fig. 16

MEDICAL DEVICES HAVING NANOPOROUS COATINGS FOR CONTROLLED THERAPEUTIC AGENT DELIVERY

TECHNICAL FIELD

This invention relates to therapeutic-agent-containing medical devices, and more particularly, to medical devices having porous coatings that control therapeutic agent release.

BACKGROUND OF THE INVENTION

The in-situ delivery of therapeutic agents within the body of a patient is common in the practice of modern medicine. In-situ delivery of therapeutic agents is often implemented using medical devices that may be temporarily or permanently placed at a target site within the body. These medical devices can be maintained, as required, at their target sites for short or prolonged periods of time, in order to deliver therapeutic agents to the target site.

For example, in recent years, drug eluting coronary stents, which are commercially available from Boston Scientific Corp. (TAXUS), Johnson & Johnson (CYPHER) and others, have become the standard of care for maintaining vessel patency after balloon angioplasty. These existing products are based on metallic balloon expandable stents with biostable polymer coatings, which release antiproliferative drugs at a controlled rate and total dose.

Nanoporous materials have the potential to revolutionize drug delivery. For example, iMEDD, Inc. has created silicon membranes with parallel channels ranging from 4 to 50 nm. Diffusion rates of various solutes through such membranes have been measured and conform to zero-order kinetics in some instances (i.e., release is constant with time). This is in contrast with typical situations in which drug diffusion rates decay with time, because the concentration gradient, and thus the driving force for diffusion, is also decaying with time. Diffusion is ordinarily governed by Fick's law, which states that the flux of a given substance (i.e., the amount of the substance crossing a unit area per unit time) arising from molecular diffusion is directly proportional to the concentration gradient of the substance. One explanation for zero order behavior is that, by making the diameter of the nanopores only slightly larger than that of the drug, the nanopores act as bottlenecks, forcing the drugs to proceed in a substantially single-file fashion through the membrane. iMedd claims that the membranes can be engineered to control rates of diffusion by adjusting channel width in relation to the size of solutes. When the proper balance is struck, zero-order diffusion kinetics is possible. iMedd has produced a drug delivery device which consists of a drug-filled enclosure which is fitted with a nanoporous membrane as the only connection between the internal reservoir of the device and the external medium.

SUMMARY OF THE INVENTION

According to an aspect of the invention, medical devices are provided which include a substrate, at least one porous reservoir containing at least one therapeutic agent disposed over the substrate, at least one nanoporous layer disposed over the at least one porous reservoir, and at least one plugged aperture, which may be located within the substrate, within the nanoporous layer, or both.

According to another aspect of the invention, a method of forming a medical device is provided which includes (a) forming a porous reservoir over a substrate, (b) forming a nanoporous layer over the porous reservoir, (c) forming an aperture within the substrate or the nanoporous layer, (d) filling the porous reservoir with therapeutic agent through the aperture, and (d) plugging the aperture.

An advantage of the present invention is that medical devices may be provided, in which the release of therapeutic agents is tightly controlled.

Another advantage of the present invention is that medical devices with nanoporous, release-regulating layers may be provided, in which it is not necessary to pass therapeutic agent through the nanoporous layers when loading the medical devices with the therapeutic agent.

These and other embodiments and advantages of the present invention will become immediately apparent to those of ordinary skill in the art upon review of the Detailed Description and Claims to follow.

BRIEF DESCRIPTION OF THE DRAWINGS

FIGS. 11-14 are schematic cross-sectional views of the medical devices of FIGS. 3-6, respectively, after the introduction of therapeutic agents and a plug forming materials.

FIGS. 15 and 16 are partial schematic cross-sectional views of medical devices of FIGS. 7 and 8, respectively, after the introduction of therapeutic agents and a plug forming materials.

DETAILED DESCRIPTION

According to an aspect of the invention, medical devices are provided which include a substrate, at least one porous reservoir that contains at least one therapeutic agent disposed over the substrate, at least one nanoporous layer disposed over the at least one porous reservoir, and at least one plugged aperture, which may be located within the substrate, within the nanoporous layer, or both.

Examples of medical devices benefiting from the present invention vary widely and include implantable or insertable medical devices, for example, catheters (e.g., urological catheters or vascular catheters such as balloon catheters and various central venous catheters), guide wires, balloons, filters (e.g., vena cava filters and mesh filters for distil protection devices), stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts), vascular access ports, dialysis ports, embolization devices including cerebral aneurysm filler coils (including Guglilmi detachable coils and metal coils), septal defect closure devices, myocardial plugs, patches, pacemakers, lead coatings including coatings for pacemaker leads, defibrillation leads, and coils, ventricular assist devices including left ventricular assist hearts and pumps, total artificial hearts, shunts, valves including heart valves and vascular valves, anastomosis clips and rings, cochlear implants, tissue bulking devices, and tissue engineering scaffolds for cartilage, bone, skin and other in vivo tissue regeneration, sutures, suture anchors, tissue staples and ligating clips at surgical sites, cannulae, metal wire ligatures, urethral slings, hernia "meshes", artificial ligaments, orthopedic prosthesis such as bone grafts, bone plates, joint prostheses, orthopedic fixation devices such as interference screws in the ankle, knee, and hand areas, tacks for ligament attachment and meniscal repair, rods and pins for fracture fixation, screws and plates for craniomaxillofacial repair, dental implants, or other devices that are implanted or inserted into the body and from which therapeutic agent is released or accessed.

Thus, while the devices of the invention in some embodiments may simply provide for controlled release of one or more therapeutic agents as a dosage form, in other embodiments, the medical devices of the invention are configured to provide a therapeutic function beyond controlled species transport, for instance, providing mechanical, thermal, magnetic and/or electrical functions within the body, among other many possible functions.

The medical devices of the present invention include, for example, implantable and insertable medical devices that are used for systemic treatment, as well as those that are used for the localized treatment of any mammalian tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, ears, spine, nervous system, lungs, trachea, esophagus, intestines, stomach, brain, liver and pancreas, skeletal muscle, smooth muscle, breast, dermal tissue, cartilage, tooth and bone.

As used herein, "treatment" refers to the prevention of a disease or condition, the reduction or elimination of symptoms associated with a disease or condition, or the substantial or complete elimination of a disease or condition. Preferred subjects are vertebrate subjects, more preferably mammalian subjects and more preferably human subjects.

Medical articles having sustained therapeutic agent release profiles are provided in certain embodiments of the invention. By "sustained release profile" is meant a release profile in which less than 25% of the total release from the medical article that occurs over the entire course of administration occurs after 1 day (or in some embodiments, after 2, 4, 8, 16, 32, 64, 128 or even more days) of administration. Conversely, this means that more than 75% of the total release from the medical device will occur after the device has been administered for the same period.

Substrate materials for the medical devices of the present invention may vary widely in composition and are not limited to any particular material. They can be selected from a range of biostable materials and biodisintegrable materials (i.e., materials that are dissolved, degraded, resorbed, or otherwise eliminated upon placement in the body), including (a) organic materials (i.e., materials containing organic species, typically 50 wt % or more) such as polymeric materials (i.e., materials containing polymers, typically 50 wt % or more polymers) and biologics, (b) inorganic materials (i.e., materials containing inorganic species, typically 50 wt % or more), such as metallic materials (i.e., materials containing metals, typically 50 wt % or more) and non-metallic inorganic materials (e.g., including carbon, semiconductors, glasses and ceramics, which may contain various metal- and non-metal-oxides, various metal- and non-metal-nitrides, various metal- and non-metal-carbides, various metal- and non-metal-borides, various metal- and non-metal-phosphates, and various metal- and non-metal-sulfides, among others), and (c) hybrid materials (e.g., hybrid organic-inorganic materials, for instance, polymer/metallic inorganic and polymer/non-metallic inorganic hybrids).

Specific examples of non-metallic inorganic materials may be selected, for example, from materials containing one or more of the following: metal oxides, including aluminum oxides and transition metal oxides (e.g., oxides of titanium, zirconium, hafnium, tantalum, molybdenum, tungsten, rhenium, iron, niobium, and iridium); silicon; silicon-based ceramics, such as those containing silicon nitrides, silicon carbides and silicon oxides (sometimes referred to as glass ceramics); calcium phosphate ceramics (e.g., hydroxyapatite); carbon; and carbon-based, ceramic-like materials such as carbon nitrides.

Specific examples of metallic inorganic materials may be selected, for example, from metals such as gold, iron, niobium, platinum, palladium, iridium, osmium, rhodium, titanium, tantalum, tungsten, ruthenium, and magnesium, among others, and alloys such as those comprising iron and chromium (e.g., stainless steels, including platinum-enriched radiopaque stainless steel), alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N), alloys comprising cobalt, chromium, tungsten and nickel (e.g., L605), alloys comprising nickel and chromium (e.g., inconel alloys), and biodisintegrable alloys including alloys of magnesium and/or iron (and their alloys with combinations of Ce, Ca, Zn, Zr and Li), among others.

Specific examples of organic materials include polymers (biostable or biodisintegrable) and other high molecular weight organic materials, and may be selected, for example, from suitable materials containing one or more of the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polyether-block co-polyamide polymers (e.g., Pebax® resins), polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, vinyl aromatic polymers and copolymers such as polystyrenes, styrene-maleic anhydride copolymers, vinyl aromatic-hydrocarbon copolymers including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); polyesters including polyethylene terephthalates, polybutylene terephthalates and aliphatic polyesters such as polymers and copolymers of lactide (which includes lactic acid as well as d-, l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, and glycosaminoglycans such as hyaluronic acid; as well as blends and further copolymers of the above.

In the medical devices of the present invention, transport of therapeutic agents from the therapeutic-agent-containing porous reservoirs is regulated by the nanoporous layers that are disposed over the porous reservoirs. The nanoporous layers may contain individual pores (e.g., parallel pores), they may contain interconnected pores, or both. The pores may be regular (e.g., cylindrical, hexagonal, etc.) or irregular in geometry. They may change shape and\or cross-sectional dimension over the length of the pore (e.g., bottle-shaped pores, cone-shaped pores, etc.). As used herein, a "nanoporous" layer is one that contains nanopores. The nanoporous layers of the invention typically have a porosity of 0.4 or greater.

Figure 1:
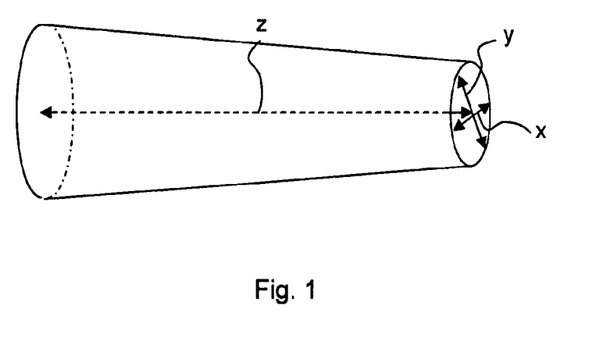
FIG. 1 is a schematic illustration of an idealized pore.

As used herein, "nanopore" is a void having a minimal cross-sectional dimension (e.g., minimal pore width) that does not exceed 50 nm in length. As used herein, nanopores include "micropores," which are smaller than 2 nm in cross-sectional dimension and "mesopores," which range from 2 to 50 nm in cross-sectional dimension. As used herein, "macropores" are larger than 50 nm in cross-sectional dimension and are thus not nanopores. By way of example, an idealized conical nanopore is illustrated in FIG. 1. Being a nanopore, the pore of FIG. 1 has a minimal cross-sectional dimension (in this instance, the orthogonal dimensions "x" and "y," each of which correspond to the width of the nanopore) that does not exceed 50 nm in length. The third orthogonal dimension "z" of the cylindrical pore of FIG. 1 can be of any length and thus can be greater than 50 nm in length. Nanoporous layers may further comprise some pores that are not nanopores. For example, nanoporous materials may contain macroporous voids interconnected with short nanoporous connections.

Porous layers, including nanoporous layers may be formed using a variety of techniques. Pores sizes may range, for example, from pores on the order of 1 nm (e.g., for zeolites of aluminum oxides) to pores on the order of 1 μm (e.g. for sol-gel materials) or larger.

In some embodiments of the invention, pore size may vary within the thickness of the nanoporous layer, for example, varying in a stepwise or gradual (gradient) fashion. For instance, such a layer may have a pore size that is smaller its upper surface than at the interface with the porous reservoir. For instance, where the nanoporous layer is formed from a biodegradable material that erodes from the upper surface (e.g., a biodegradable metal such as magnesium), this may result in an increase in therapeutic agent release over time.

As another example, such a layer may have a pore size that is smaller its upper surface than at the interface with the porous reservoir. For instance, the smaller pore size at the lower interface may be used to control release of therapeutic agent disposed beneath the nanoporous layer within the porous reservoir, whereas the larger pore size at the upper surface may allow the pores to be filled with additional therapeutic agent to create an initial burst in release. Such a structure may be created, for example, by conducting an isotropic etching step (e.g., using a liquid or dry etch process) from the surface, which would make the pores wider at the top than at the bottom.

Depending on the pore size, it is known that nanoporous layers having parallel or near parallel pore structures can release species such as therapeutic agents in accordance with zero order kinetics. In some instances, the lateral dimensions (e.g., the radii) of the interconnected pores approach the lateral dimensions (e.g., the hydrated radius) of the species that is being transported. Consequently, the species may move within, and ultimately be released from, pores of these diameters (as opposed to being trapped by pores having smaller diameters). Under such circumstances, the interactions between the species and the walls of the nanopores will have a significant effect upon the transport that is observed. Indeed, as the diameter of the pore approaches the diameter of the species that is being transported, the surface interactions begin to dominate transport. See, e.g., Tejal A. Desai, Derek Hansford and Mauro Ferrari, "Characterization of micromachined silicon membranes for immunoisolation and bioseparation applications" J. Membrane Science, 159 (1999) 221-231, which describes insulin release through silicone nanomembranes. In other less-structured nanoporous layers, the species may travel through the region via interconnected networks of pores. As with parallel pore structures, the interconnected pore structures are capable of transporting species in a highly controlled manner, and they have the potential to approach zero order transport kinetics where pore diameters approach the size of the species that is being transported. The transport rate may also be affected by the tortuousity of the interconnected pores and the thickness of the layer.

For example, in F. Martin et al., *Journal of Controlled Release,* 102 (2005) 123-133, diffusion kinetics of various solutes were measured across silicon-based membranes having arrays of uniform channels. Non-Fickian behavior was observed as channel width approached the hydrodynamic diameter of the solute. (As noted above, molecular diffusion is ordinarily governed by Fick's law—when this law is not followed, the behavior is deemed "non-Fickian.") Zero-order diffusion, which is clearly non-Fickian, was observed at a channel width of 20 nm for interferon, and the same phenomenon was observed with albumin (BSA) at a channel width of 13 nm. Albumen demonstrated Fickian diffusion kinetics at channel widths of 26 nm and larger. Albumin has a molecular weight of about 66 kdaltons. For larger proteins, such as those having a molecular weight up to 700 kdaltons (e.g., proteins which are about 10 times as heavy and about 2.15 times larger in diameter), one would expect a zero-order release for channels up to on the order of 26 nm. Specifically, following the logic that zero-order diffusion goes hand in hand with the molecular size, one would it expect that a molecule with a diameter that is 2.15 times the size of albumin would have zero order release at roughly 2 times the pore sizes for which Albumin follows this behavior (e.g., 13 nm). This, of course, will depend on various other factors, including the particular molecular shape of the protein (the above estimate assumes a spherical shape).

Nanopores are also known to promote cell adhesion. See, e.g., E. E. L. Swan, K. C. Popat, C. A. Grimes, T. A. Desai, "Fabrication and evaluation of nanoporous alumina membranes for osteoblast culture," *Journal of Biomedical Materials Research Part A*, Volume 72A, Issue 3, Pages 288-295, Published Online: 14 Jan. 2005, which describes osteoblast response to surface topography in anodized nanoporous alumina membranes.

The thickness of the nanoporous layers for use in the present invention may vary widely, with typical layer thicknesses ranging, for example, from 100 nm to 200 nm to 500 nm to 1 µm to 2 µm, among other values.

The pores of the porous reservoirs are generally substantially larger (e.g., 10 to 30 to 100 to 300 to 1000 or more times larger) than those of the nanoporous layers, and they are typically interconnected, thereby allowing for efficient movement of therapeutic agents within the same. For example, efficient movement within the porous reservoirs allows them to be readily loaded with therapeutic agent. There is generally no upper limit to pore size within the porous reservoirs, so long as they are capable of supporting one or more overlying layers, including at least one nanoporous layer. Typical pore widths for porous reservoirs in accordance with the invention include those ranging from less than 10 nm to 100 nm to 1 µm to 10 µm or more. For example, porous reservoirs may be made using polystyrene templates ranging from 10 nm to 10 micrometer in size. Gi-Ra Yi et al., "Ordered Macroporous Particles by Colloidal Templating," *Chem. Mater.,* 2001, 13, 2613-2618.

In general, the greater the volume of the porous reservoir, the greater the amount of therapeutic agent that can be loaded into the same. Reservoir volume may be increased, for example, by increasing the area of the substrate that is covered by the porous reservoir, up to and including the entire substrate surface. Reservoir volume may also be increased, for example, by increasing the thickness of the porous reservoir. Thickness of the porous reservoirs may vary widely, with typical thicknesses ranging from 100 nm to 1 µm to 10 µm to 100 µm or more. Porous reservoirs may be formed, for example, by stacking multiple (e.g., 2 to 3 to 5 to 10 or more) layers on one another, allowing one to readily tailor porous reservoir thickness.

Layer stacking also allows one to, for example, create structures containing multiple porous reservoirs, which may have the same or different pore sizes, separated by nanoporous layers, which may also have the same or differing pore sizes. This may be used, for example, to achieve zero order release from a smaller therapeutic agent at the same time as a larger therapeutic agent. For instance one may provide a smaller therapeutic agent in a first porous reservoir, covered by a first nanoporous layer having a pore size that is sufficient to achieve non-Fickian release (e.g., zero-order or near-zero-order release) of the smaller therapeutic agent, over which is disposed a second porous reservoir containing a larger therapeutic agent, covered by a second nanoporous layer having a pore size that is sufficient to achieve non-Fickian release of the larger therapeutic agent. Unlike the larger therapeutic agent, movement of the smaller therapeutic agent is not substantially restricted by the second nanoporous layer. Of course, the second porous reservoir and second nanoporous layer may be placed adjacent to (rather than on top of) the first porous reservoir and first nanoporous layer to achieve a similar effect.

As with substrate materials, nanoporous layers and porous reservoirs for use in the present invention may vary widely in composition and are not limited to any particular material. They can be selected from a wide range of biodisintegrable and biostable materials, such as suitable members of the organic and inorganic materials listed above, including polymeric, metallic, and non-metallic inorganic materials, as well as hybrids of the same, among others.

Several examples of techniques which may be employed for forming porous regions (e.g., nanoporous layers, porous reservoirs, or both) are summarized below. These and other known techniques may be used to produce porous regions in which the pore size (e.g., pore width) can be from as little as about 0.3 nm to 1 nm to 3 nm to 10 nm to 30 nm to 300 nm to 1 µm to 3 µm to 10 µm to 30 µm to 100 µm or larger. Where the pore sizes are in the nanometer range, pore forming techniques frequently exploit thermodynamic forces to drive the porous structures to an ordered state, including hexagonal porous structures, cubic porous structures, and many others.

In many techniques, a precursor region is formed, which is subsequently converted into a porous layer. For example, a mask with appropriately scaled apertures may be formed on a precursor region using known lithographic techniques, including optical, ultraviolet, deep ultraviolet, electron beam, and x-ray lithography, and subjected to further processing (e.g., wet or dry etching). For instance, a process for forming nanoporous silicon is described in L. Leoni, D. Attiah and T. A. Desai, "Nanoporous Platforms for Cellular Sensing and Delivery," *Sensors,* 2002, 2, 111-120.

In some embodiments, a precursor region is initially formed which comprises two or more materials. Subsequently, the precursor region is subjected to conditions where at least one material is either reduced in volume or eliminated from the precursor region. By providing domains of such material within the precursor region, a porous layer may be formed. Materials for forming such removable or size-reducible domains include (a) materials that are converted into gaseous species upon heating, for example, materials that sublime, materials that melt and evaporate, and materials that form gaseous reaction products such as combustible materials, (b) metal oxides which may be reduced to their corresponding metal, resulting in a loss in volume, and (c) materials which are dissolved or otherwise removed in a solution, among other examples.

Some of these techniques rely on the ability of certain materials to phase separate into nanodomains. For example, nanoporous layers may be produced from metal alloys of this type, which contain two or more phase-separated metals of differing nobility. Upon removing at least one of the less noble metals (e.g., by oxidation and removal), a nanoporous layer is formed. Further details concerning such de-alloying processes can be found, for example, in J. Erlebacher et al., "Evolution of nanoporosity in de-alloying," *Nature*, Vo. 410, 22 Mar. 2001, 450-453; A. J. Forty, "Corrosion micromorphology of noble metal alloys and depletion gilding," *Nature*, Vol. 282, 6 Dec. 1979, 597-598; R. C. Newman et al., "Alloy Corrosion," *MRS Bulletin*, July 1999, 24-28; and U.S. Patent App. Pub. No. 2004/0148015 assigned to Setagon.

Nanopores may also be formed based on the self-assembly of nanodomains using block copolymers. Cylindrical nanopores may be formed, for example, using diblock copolymers composed of polymethylmethacrylate (PMMA) and polystyrene (PS). The molecular weight and volume fraction of styrene may be selected such that the copolymer self-assembles into arrays of PMMA cylinders hexagonally packed in a PS matrix. The PMMA cylinders are then removed yielding a PS film with ordered nanopores. For further information, see, e.g., H. X. He and N. J. Tao, "Electrochemical fabrication of metal nanowires" in Encyclopedia of Nanoscience and Nanotechnology, Eds., N. S. Nalwa, American Scientific Publishers, 2003, and the references cited therein. See also Pub. No. US 2006/0171985 to Richard et al., in which phase separated polymeric regions are described that include (a) at least one biostable polymeric phase and (b) at least one biodisintegrable polymeric phase that is of nanoscale dimensions. The biodisintegrable polymeric phase is then subjected to suitable processing conditions (e.g., conditions that promote hydrolysis or other chemical breakdown of the biodisintegrable polymeric phase) in order to yield a nanoporous region.

A variety of procedures are also known for the production of porous ceramic structures, many of which are self-assembly-based techniques that require an alignment template about which the ceramic material is formed. Block copolymers, polymer spheres, water-in-oil emulsions, colloidal crystals and bioskeletons all are candidates for use as templates.

For example, some known processes, including various sol-gel techniques, utilize block copolymers as templates in the creation of ceramic-polymer hybrid structures. The block copolymers are subsequently removed from the hybrid structures, for example, by thermal and/or chemical processes (e.g., by burning out the copolymer or by exposing the copolymer to a solvent), leaving behind porous ceramic structures, including mesoporous and macroporous structures. (Mesoporous regions are defined herein as porous regions having an average pore size ranging from 2-50 nanometers, and macroporous regions are defined herein as porous regions having an average pore size ranging from 50 nanometers to 5 microns or larger.) For example, high porosity, uniform pore size mesoporous silicon oxide and aluminum oxide films may be prepared by sol-gel methods using block copolymers as the structure-directing agents. For example, J.-A. Paik et al. "Micromachining of mesoporous oxide films for microelectromechanical system structures," *J. Mater. Res.*, Vol. 17, No. 8, August 2002, 2121 have reported the formation of films that are over 50% porous with uniform pores of 8-nm average diameter.

Other methods of forming porous ceramic structures involve the formation of a colloid that contains (a) ceramic nanopowder and (b) organic spheres, for example, polymer spheres, having a specified diameter as template particles. The powder fills in around the spheres when the liquid portion of the colloid is evaporated. Subsequently, the organic spheres are removed (e.g., thermally or chemically) to create a porous structure. This process has been successfully used, for example, to form 300 nanometer pores in titania, silica and alumina structures, which have overall dimensions on the order of several millimeters. The shrinkage that is observed using this method is much lower than with typically sol gel processes (e.g., 6 percent versus 30 percent for a typical sol gel process). For further information, see, e.g., Gi-Ra Yi et al., "Ordered Macroporous Particles by Colloidal Templating," *Chem. Mater.*, 2001, 13, 2613-2618.

In some embodiments of the invention, different porosities are created using templates of different dimensions.

Other techniques for the formation of porous structures do not require the use of templates. For example, Singh et al. have investigated various parameters (e.g., the effects of sol concentration, water/acid addition, and humidity conditions) that influence the self-assembled fabrication of nanoporous ceramic films using sol-gel processing. More specifically, a sol-gel process was used to prepare the titania films, without a block copolymer or other template, and parameters such as those above were varied to test the effects. Through their efforts, they were able to produce a variety of nanoporous films. See, e.g., Singh, R. S., Grimes, C. A., Dickey, E. C. "Fabrication of nanoporous $TiO_2$ films through Bernard-Marangoni convection" *Materials Resources Innovations*. Aug. 18, 2001.

Dr. Abdelkrim Chemseddine from Hahn-Meitner Institut has also fabricated nanostructured materials through wet and sol-gel chemistries. His primary work is focused on the formation of nanostructured semiconducting films for use in solid state injection fuel cells. He has developed hexagonal and cubic nanoporous titania structures having pore sizes on the order of 6 nm. See, e.g., http://www.hmi.de/people/chemseddine/group.htm for more information.

See also, U.S. Pat. No. 6,399,528 entitled "Porous aluminum oxide structures and processes for their production," which describes various ways to produce different pore sizes in alumina.

In some embodiments, porous layers are formed using vapor deposition techniques. For example, two or more metals may be simultaneously deposited via physical vapor deposition (PVD) (e.g., by sputtering separate targets of a single metal or by sputtering a single target containing multiple metals), followed by annealing if necessary to cause phase separation, which is followed by de-alloying, for example, using techniques such as those described above.

Some embodiments of the invention employ chemical vapor deposition (CVD) techniques, including low-pressure chemical vapor deposition (LPCVD) processes and plasma-enhanced chemical vapor deposition (PECVD) processes, in the formation of nanoporous layers. For example, it is known to deposit nanoporous silicon dielectric films (e.g., silicon oxide films such as silicon dioxide) by PECVD using organosilicate precursor compounds such as tetraethylorthosilicate (TEOS), typically in the presence of an oxidant such as $N_2O$, $O_2$, $O_3$, $H_2O_2$, etc. See e.g., United States Patent Application No. 2002/0142579 to Vincent et al. As another example, it is known to deposit nanoporous silicon oxycarbide films (specifically SiOCH, also known as hydrogenated silicon oxycarbide) by PECVD oxidation of $(CH_3)_3SiH$ in the presence of an oxidant (i.e., $N_2O$). See, e.g., D. Shamiryan et al., "Comparative study of SiOCH low-k films with varied porosity interacting with etching and cleaning plasma," *J. Vac. Sci. Technol. B*, 20(5), September/October 2002, pp. 1923-1928.

As another example, in hot-filament CVD (HFCVD), also known as pyrolytic or hot-wire CVD, a precursor gas is thermally decomposed by a resistively heated filament. The resulting pyrolysis products then adsorb onto a substrate maintained at a lower temperature (typically around room temperature) and react to form a film. One advantage associated with pyrolytic CVD is that the underlying substrate can be maintained at or near room temperature. For example, in some embodiments, fluorocarbon polymer film and fluorocarbon-organosilicon copolymer films are prepared. Due to the nucleation and growth mechanisms in the HFCVD processes, nanoporous films can be made using HFCVD. For further information, see, e.g., United States Patent Application No. 2003/0138645 to Gleason et al., U.S. Pat. No. 6,156,435 to Gleason et al., and K. K. S. Lau et al., "Hot-wire chemical vapor deposition (HWCVD) of fluorocarbon and organosilicon thin films," *Thin Solid Films*, 395 (2001) pp. 288-291.

In still other embodiments, nanoporous layers are formed using electrochemical methods. For example, materials with nanodomains may be formed by first incorporating suspended nanoparticles into a matrix that is formed by electrodeposition and/or electroless deposition. (For example, nanoparticles that are dispersed by adsorbing cations on their surfaces, are known to travel to the cathode where electrodeposition takes place, such that the nanoparticles are incorporated into the deposited layer.). Once formed, such nanodomains are subsequently reduced in size as discuss above (e.g., by sublimation, evaporation, combustion, dissolution, etc.).

Further information on porous layers and methods for making them can be found, for example, in U.S. Patent App. Pub. Nos. 2005/0208100, 2006/0129215, 2006/0127443, and the references therein.

By selecting a suitable method from those described above, among others, porous materials having a wide range of pore sizes and porosities may be formed on a wide range of underlying materials.

In some embodiments of the invention, a porous layer (corresponding to the porous reservoir) is first formed on a substrate, for example, by direct formation of a porous layer (e.g., via a deposition, etc.) or by the formation of a precursor layer which is subsequently processed (e.g., by removing a material, etc.) to produce a porous region. This step is then followed the formation of a nanoporous layer, either directly or via a precursor layer.

In other embodiments, a precursor layer (corresponding to the porous reservoir) is formed, over which a nanoporous layer is directly formed (e.g., via deposition, etc.). Subsequently, the underlying precursor region is processed to produce the porous reservoir. Where a material is removed from the precursor layer to form the porous reservoir (e.g., by sublimation, evaporation, combustion, dissolution, etc.), the material may pass through the nanoporous region or the material may pass through one or more apertures in the nanoporous layer, the underlying substrate, or both, to the extent that such apertures have been formed at the time of material removal.

In still other embodiments, a precursor layer (corresponding to the porous reservoir) is formed, over which a further precursor layer (corresponding to the nanoporous layer) is formed. Subsequently, both precursor layers are processed to produce the porous reservoir and the nanoporous layer. To the extent that the two precursor layers are processed under the same conditions of produce porous layers (e.g., where they are formed using organic spheres of the same material, but of different diameter), they may be processed simultaneously. Otherwise, the precursor layers may be processed sequentially. As above, where a material is removed to form the porous reservoir (e.g., by sublimation, evaporation, combustion, dissolution, etc.), the material may pass through the nanoporous region or the material may pass through one or more apertures, to the extent that such apertures have been formed at the time of processing.

In yet other embodiments, a nanoporous layer is formed within a porous layer that corresponds to the porous reservoir. For example, a macroporous layer (corresponding to the porous reservoir) may first be formed, after which one partially closes the pores near the upper surface to create a nanoporous layer.

One could create a macroporous layer, for example, using sol-gel processing, followed by introduction of material into the pores near the upper surface of the macroporous layer to partially close the pores of the macroporous layer, for instance, by applying nanoparticles suspended in a high viscosity polymer solution. For example, one may first create a macroporous layer with rather large pores which one can readily fill with a polymeric substance (e.g., by repeated dip-coating). After the polymer has penetrated and filled most or all of the porous layer (e.g., where an excellent solvent for the polymer is employed), one removes the very top layer of the polymer by flushing it with a solvent, which dissolves only the polymer that lies near the upper surface of the macroporous layer, while leaving more deeply buried polymer within of the porous layer. For example, one may use the same solvent that is used to initially penetrate the polymer layer or one may use a solvent which only poorly dissolves the polymer. The latter approach would take off only the topmost layer of the polymer, leaving behind most of the polymer deeper inside of the porous layer. One may then make a solution of nanoparticles and fill the now open topmost portion of the porous layer. Once this is done, one removes the buried polymer with a heat treatment step and fuses at the same time the nanoparticles onto the topmost portion of the porous layer, thereby creating a nanoporous layer within the upper portion of the macroporous layer. This is particularly useful where the nanoparticles and the macroporous layer are formed from the same material. To make the fill openings, one may, for example, place one or more polymer dots on the macroporous coating just before filling the topmost portion of structure with the nanoparticle solution, ensuring that one or more areas will be not be filled with the nanoparticle solution.

As an alternative to nanoparticles, after taking away the top layer of the polymer filling, one may use a pulsed laser deposition technique to partially fill the top layer with the same material that the original macroporous coating layer was formed from, thereby reducing the pore size.

As another example, a portion of a macroporous layer formed from a malleable material such as a metal may be converted to a nanoporous layer by using a laser shock peening process to reduce the pore size very locally. Briefly, when a laser pulse is directed at the macroporous surface under water, the ablated fluid locally creates a pressure wave which is directed mainly in the direction of the macroporous surface, compressing the material of the macroporous layer and reducing the pore size at the surface. See, e.g., C. S. Montross et al., "Laser shock processing and its effects on microstructure and properties of metal alloys: a review," *International Journal of Fatigue* 24 (2002) 1021-1036. Such a process may be performed as follows: A first macroporous layer is made and covered with a laser absorbing layer (e.g., a carbon filled polymer). After the laser processing has been performed under water, one then removes the remaining laser absorbing layer, for example, by dissolving or heat treatment. Because substantial pressures are generated during laser processing, mounting a medical device such as stent on a mandrel may be advisable to prevent macroscopic deformation of the device structure.

In some embodiments, the entire surface is laser processed, except for one or more areas which are not processed so as to provide a fill opening, which can then be plugged after loading the underlying macroporous layer with a therapeutic agent. Conversely, the macroporous layer may be loaded with therapeutic agent prior to laser processing the entire surface, thereby eliminating the need for any fill openings. Because the effects of the laser processing are highly local, degradation of the therapeutic agent in the underlying macroporous due to heat effects will be minimized.

In still other embodiments, a porous reservoir may be formed beneath the upper surface of a nanoporous layer. For example, one may ablate the nanoporous region below the surface by focusing laser radiation (e.g., from an excimer or femtosecond laser) on a sub-surface region of the nanoporous layer, thereby increasing the pore size and porosity of the same. The gases produced by the ablation process can escape through the interconnected pores of the upper nanoporous region, which is preserved.

In some embodiments, the porous reservoir and nanoporous layer may be formed from the substrate material. For example, L. Vaccari et al., *Microelectronic Engineering,* 83 (2006) 1598-1601, describe a process in which boron-doped silicon substrates are subjected to an anodization procedure to produce porous silicon, characterized by macropores of 2 µm average diameter with a 200 nm thick nanoporous coverage.

As previously indicated, in addition to having a substrate, at least one porous reservoir over the substrate, and at least one nanoporous layer over the porous reservoir, in some aspects, the medical devices of the present invention also have at least one plugged aperture, which may be found within the substrate, within the nanoporous layer, or both.

Figure 2A:
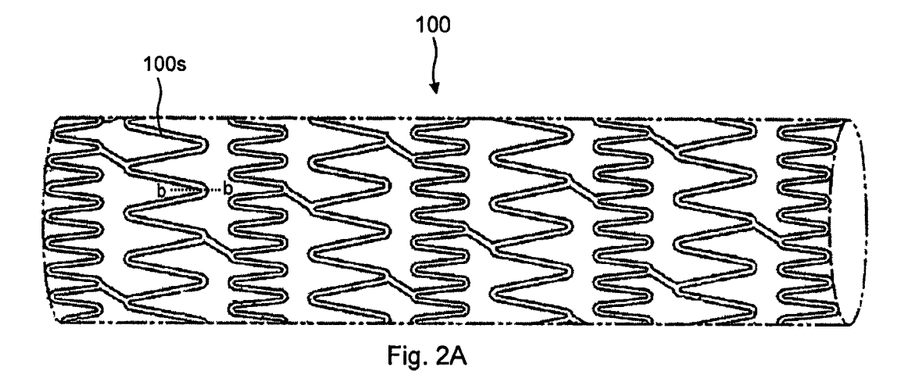
FIG. 2A is a schematic perspective view of a coronary stent, in accordance with an embodiment of the invention.
Figure 2B:
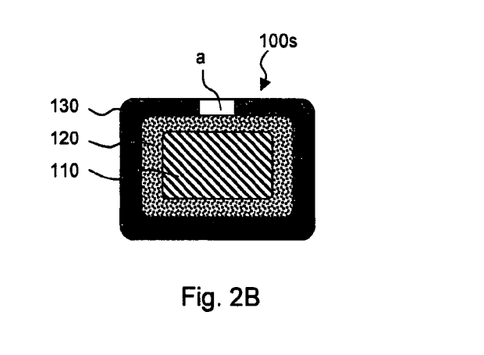
FIG. 2B is an expanded schematic cross-sectional view take along line b-b of FIG. 2A, prior to the introduction of a therapeutic agent and a plug forming material.

For further clarity, a few specific embodiments of the invention will now be discussed in conjunction with the drawings. FIG. 2A is a schematic perspective view of a vascular stent 100, in accordance with an embodiment of the invention. Stent 100 contains various stent struts 100s, as is known in the vascular stent art. FIG. 2B is a schematic cross-sectional view taken along line b-b of FIG. 2A and illustrates a stent substrate 110 (e.g., a stainless steel or nitinol substrate), a porous reservoir 120 provided over the substrate 110, and a nanoporous layer 130 provided over the porous reservoir 120. The nanoporous layer 130 contains at least one aperture a which allows a therapeutic agent to be loaded into porous reservoir 120. (As noted above, the aperture a may also assist in removing material from a precursor of the porous reservoir in some embodiments.)

As also noted above, due to the small size of the pores within the nanoporous layer 130, transport of therapeutic agent across the same is restricted. By providing one or more apertures a, however, therapeutic agent can be introduced into the porous reservoir 120 without the necessity of passing it though the nanoporous layer 130. After loading the porous reservoir 120 with therapeutic agent, the one or more apertures are plugged as described in more detail below. Loading the therapeutic agent after the nanoporous region is formed is advantageous, for example, in that it allows one to accurately measure the weight of the loaded agent.

As an alternative, one could load the porous reservoir before applying the nanoporous layer over the porous reservoir (or before forming the nanoporous layer within the porous reservoir as described above). In this case, the processes for producing the nanoporous layer should employ conditions which are compatible with the substantial retention and preservation of the therapeutic agent.

In the embodiment illustrated in FIGS. 2A and 2B, the nanoporous layer 130 encapsulates both the porous reservoir 120 and the substrate 100. In other embodiments, the nanoporous layer 130 and the substrate 100 cooperate to surround the porous reservoir 120.

Figure 3:
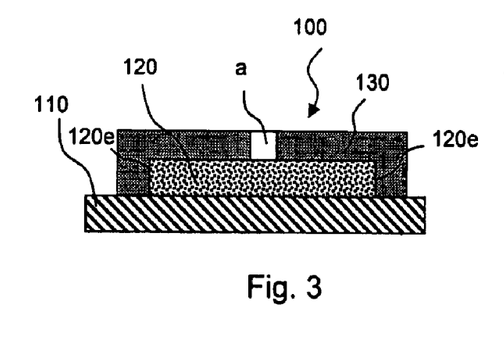
FIGS. 3-6 are schematic cross-sectional views of medical devices in accordance with various embodiments of the invention, prior to the introduction of therapeutic agents and plug forming materials.

For example, the cross section of FIG. 3 shows a medical device substrate 100 (which may be a cross-section of a stent strut or of another medical device substrate), a porous reservoir 120 provided over the substrate 110, and a nanoporous layer 130 provided over the porous reservoir 120. The nanoporous layer 130 contains at least one aperture a. Note that in the embodiment shown in FIG. 3, the lateral extent of the nanoporous layer 130 is greater than that of the porous reservoir 120 so that the edges 120e of the porous reservoir 120 are covered. Such edges 120e would otherwise provide a low resistance path for therapeutic agent release.

Figure 4:
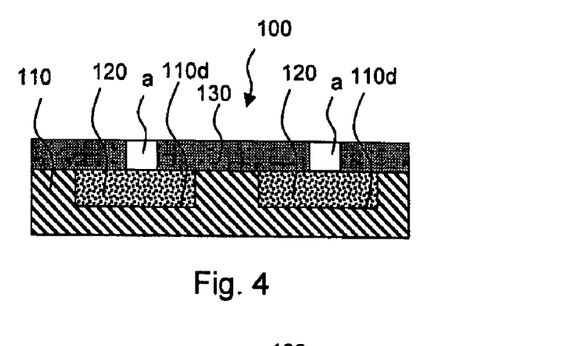

In another example, the cross section of FIG. 4 shows a medical device substrate 100, two porous reservoirs 120 provided in depressions 110d formed in the substrate 110, and a nanoporous layer 130 provided over the porous reservoirs 120 and the substrate 110. The porous reservoirs 120 may have the same or different pore sizes. The nanoporous layer 130 contains apertures a. As in FIG. 3, the nanoporous layer 130 and the substrate 100 cooperate to surround the porous reservoirs 120. While a single nanoporous layer 130 is disposed over the porous reservoirs 120 of FIG. 4, as an alternative, each reservoir could be provided with its own nanoporous layer, thereby making it possible to tailor the pore size of each nanoporous layer to the therapeutic agent that is loaded into the porous reservoir below it.

Porous reservoirs in accordance with the present invention (and depressions that they may occupy, in certain embodiments) may come in a variety of shapes and sizes. Examples include porous reservoirs (and depressions) whose lateral dimensions are circular, oval, polygonal (e.g., triangular, rectangular, pentagonal, etc.) as well as various other regular and irregular shapes and sizes. Multiple porous reservoirs (and depressions) can be provided in a near infinite variety of arrays. Further examples of porous reservoirs (and depressions) include elongated structures (e.g., ridges and trenches), which may be linear, which may be formed from segments whose direction undergoes an angular change (e.g., zigzag and wavy structures), which may intersect at right angles (or other angles) thereby forming grids, as well as other regular and irregular elongated structures.

Figure 5:
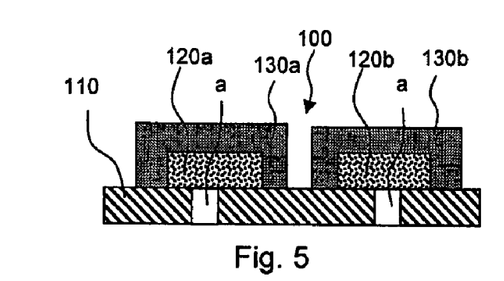

In certain embodiments of the invention, access to the porous reservoir is made via apertures a that are formed in the substrate, rather than (or in addition to) in the nanoporous layer. For example, the cross section of FIG. 5 illustrates a medical device substrate 100, two porous reservoirs 120a, 120b provided over the substrate 110, and two nanoporous layers 130a, 130b provided over the porous reservoirs 120. The nanoporous layers 130a, 130b may have the same or different pore sizes (as can the porous reservoirs 120). The nanoporous layers 130a, 130b and the substrate 100 cooperate to surround the porous reservoirs 120a, 120b. The substrate 110 contains apertures a, which provide access to the porous reservoirs 120a, 120b. As in FIG. 3, the nanoporous layers 130a, 130b extend laterally beyond the porous reservoirs 120a, 120b so that the edges of the porous reservoirs

120a, 120b are covered. In an alternative embodiment, a single nanoporous layer could be disposed over both porous reservoirs 120a, 120b.

Figure 6:
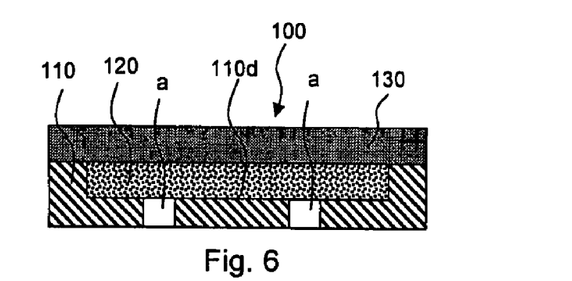

In another embodiment, the cross section of FIG. 6 shows a medical device substrate 100, a porous reservoir 120 provided within depressions 110d that are formed in the substrate 110, and a nanoporous layer 130 provided over the porous reservoir 120 and the substrate 110. The nanoporous layer 130 and the substrate 100 cooperate to surround the porous reservoir 120. The substrate 110 in FIG. 6 contains multiple apertures a, in order to provide access to the porous reservoir 120.

Figure 7:
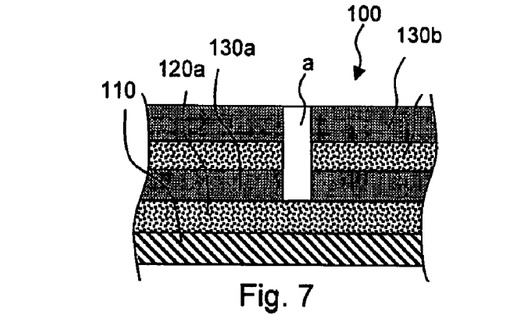
FIGS. 7 and 8 are partial schematic cross-sectional views of medical devices in accordance with various embodiments of the invention, prior to the introduction of therapeutic agents and plug forming materials.

Just as multiple porous reservoirs (and multiple nanoporous layers) may be disposed laterally along the medical device surface, so may they be stacked on top of one another. For example, the cross section of FIG. 7 shows a medical device substrate 100, a lower porous reservoir 120a disposed over the substrate (which may be, for example, provided on the substrate surface as in FIG. 3 or which may be provided within depressions as in FIG. 4), a lower nanoporous layer 130a provided over the lower porous reservoir 120a, an upper porous reservoir 120b over the lower nanoporous layer 130a, and an upper nanoporous layer 130b provided over the upper porous reservoir 120b. Access to the lower porous reservoir 120a and the upper porous reservoir 120b is provided by aperture a, which extends through the upper nanoporous layer 130b, the upper porous reservoir 120b and the lower nanoporous layer 130a.

Figure 8:
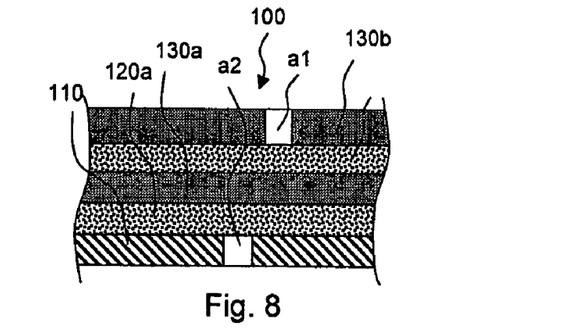

As another example, the cross section of FIG. 8 illustrates a medical device substrate 100, a lower porous reservoir 120a over the substrate, a lower nanoporous layer 130a over the lower porous reservoir 120a, an upper porous reservoir 120b over the lower nanoporous layer 130a, and an upper nanoporous layer 130b provided over the upper porous reservoir 120b. Access to the upper porous reservoir 120b is provided by aperture a1 in upper nanoporous layer 130b, whereas access to the lower porous reservoir 120a is provided by aperture a2 in substrate 110. Thus, in contrast to FIG. 7, multiple apertures a1 and a2 are used to provide independent access to the lower and upper porous reservoirs 120a, 120b.

As seen from the above, in some aspects of the invention, apertures may be formed in nanoporous layers, in substrates, or both, in order to improve drug loading (and to assist in the removal of material from a porous reservoir precursor in some embodiments). In this regard, the apertures are sized to allow the underlying reservoir to be readily filled with drug. For example, as discussed further below, a therapeutic agent in liquid form may be introduced into the apertures by any of a number of techniques, and the aperture size required, particularly the minimal aperture size, may depend on the filling technique that is employed.

Figure 9A:
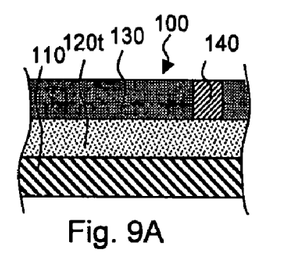
FIGS. 9A-9D are partial schematic cross-sectional views of medical devices in accordance with various embodiments of the invention.
Figure 9B:
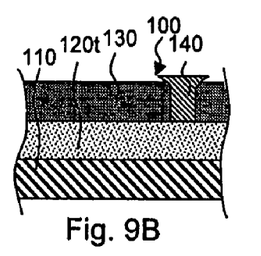
Figure 9C:
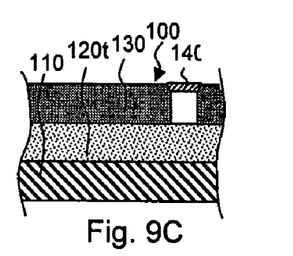
Figure 9D:
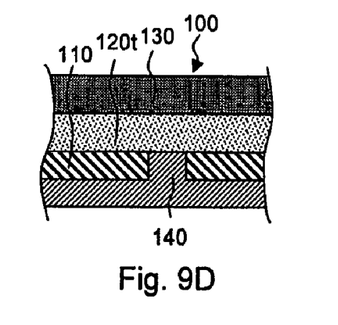
Figure 10:
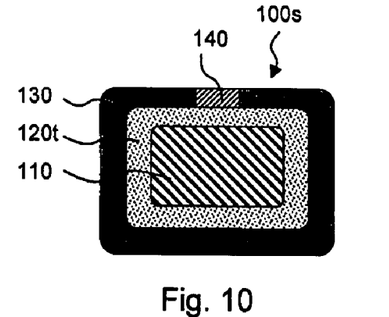
FIG. 10 is an expanded schematic cross-sectional view take along line b-b of FIG. 2A, after the introduction of therapeutic agents and a plug forming materials.
Figure 11:
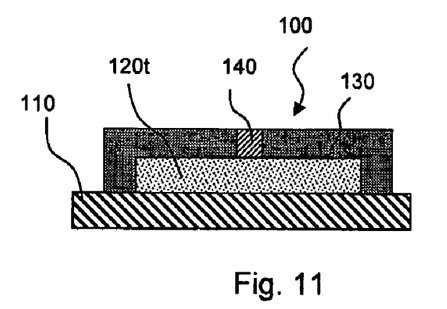

Other factors that may be taken into account when determining aperture size are those relating to the manner in which the apertures are to be plugged. For example, in some embodiments, the apertures may be completely filled with a plug forming material 140 as shown in FIG. 9A (after supplying a therapeutic agent so as to create a therapeutic-agent-containing reservoir 120t). The plug forming material 140 may in some instances overflow so as to form a "mushroom shaped" plug 140 as shown in FIG. 9B. Thus, the plug 140 may occupy only the "footprint" of the aperture or may extend laterally from the aperture, for example, ranging from 1 to 2 to 4 or more times the width of the aperture, up to and including the entire surface as illustrated in FIG. 9D. For example, it may be desirable to have the plug material cover a entire substrate surface, which may be advantageous from a processing point of view and/or where the substrate is less biocompatible than the plug material. In other embodiments, only the exterior end of the aperture is occupied by the plug forming material 140 as shown in FIG. 9C. Whether or not an aperture is filled with plug forming material will depend upon a number of factors, including the aperture diameter, the surface energy of the material within which the aperture is formed and the viscosity and surface tension of the plug forming material at the time the aperture is filled (assuming the plug forming material is a liquid), and so forth.

In other embodiments, the aperture is plugged using adjacent material (e.g., adjacent substrate material, adjacent nanoporous layer material, adjacent porous reservoir material, etc.), for instance, by localized melting or deformation.

Typical aperture widths may range, for example, from 0.5 µm to 1 µm to 2 µm to 5 µm to 10 µm to 20 µm to 50 µm to 100 µm or more in diameter. In general, the size and/or number of the apertures is not so great as to occupy so much surface area so as to significantly reduce transport through the nanoporous layer (e.g., because the plugged apertures occupy a substantial fraction of the surface of the nanoporous layer) or to significantly reduce the mechanical integrity of the device (where the plugged apertures occupy a substantial fraction of the substrate).

In some embodiments, the length and width of the aperture(s) are approximately the same. Examples include apertures whose lateral dimensions are circular, oval, polygonal (e.g., triangular, rectangular, pentagonal, etc.) as well as various other regular and irregular shapes and sizes. In other embodiments, the length may be substantially greater than width, for example, by 2 to 5 to 10 or more times.

Apertures and depressions may be formed at the time of formation of the nanoporous layer and substrate, respectively. For example, apertures may be formed by masking a portion of a porous reservoir (or precursor thereof) such that a nanoporous layer is not formed in certain areas. Mask-based techniques include those in which the masking material contacts the porous reservoir material, for example, masks formed using known lithographic techniques, including optical, ultraviolet, deep ultraviolet, electron beam, and x-ray lithography, and those in which the masking material does not contact the biodegradable material, for example, where a mask is provided between a source of nanoporous material (or a precursor thereof) and the porous reservoir (or precursor thereof) during a deposition process. As another example, substrates and nanoporous layers may be cast using molding techniques in which a mold is provided, which has one or more protrusions, which correspond to a depressions or apertures. Upon casting the material of interest, depressions or apertures are created as desired.

Apertures may also be formed by creating a nanoporous region having a region of material that is subsequently removed. For example, an aperture may be formed by including a polymer fiber which extends through the nanoporous layer (e.g., running from the substrate, from within the porous reservoir or from the surface of the porous reservoir to the nanoporous layer surface), which fiber is then removed using a suitable removal process. For instance, the nanoporous layer may be formed using a sol-gel process, and the fiber may be removed during a heat treatment process that is used to create a nanoporous ceramic layer out of the sol-gel layer.

Apertures or depressions may also be formed in existing material regions (e.g., substrates, porous reservoirs, nanoporous layers, and their precursors) using a variety of direct-write techniques, as well as mask-based techniques in which masking is used to protect material regions which are not to be excavated.

Direct write techniques include those in which excavated regions are created through contact with solid tools (e.g., microdrilling, micromachining, etc., using high precision equipment such as high precision milling machines and lathes) and those that form excavated regions without the need for solid tools (e.g., those based on directed energetic beams, for example, laser ablation). In the latter cases, techniques based on diffractive optical elements (DOEs), holographic diffraction, and/or polarization trepanning, among other beam manipulation methods, may be employed to generate direct-write patterns as desired. Using these and other techniques, many apertures and/or depressions can be ablated in a material at once. Further information on laser ablation may be found in Lippert T, and Dickinson J T, "Chemical and spectroscopic aspects of polymer ablation: Special features and novel directions," *Chem. Rev.*, 103(2): 453-485 February 2003; Meijer J, et al., "Laser Machining by short and ultrashort pulses, state of the art and new opportunities in the age of photons," *Annals of the CIRP,* 51(2), 531-550, 2002, and U.S. Pat. No. 6,517,888 to Weber.

Where laser radiation is for material excavation, manufacturing tolerances typically are on the order of the wavelength of the laser. Consequently, lasers can be focused into very small areas, allowing, for example, one to create apertures and depressions at the surface of small device components, for example, along stent struts, among many other possibilities. For example, depressions and apertures having submicron surface dimensions can be formed using known techniques. For instance, J. Bekesi et al., "Efficient submicron processing of metals with femtosecond UV pulses," *Appl. Phys. A,* 76, 355-357 (2003), describes the generation of submicron-sized holes on metal surfaces by applying femtosecond UV laser pulses. Using different optical schemes, submicron-sized holes (including blind holes and through holes) and hole patterns were ablated into metal surfaces. For example, holes having 600-nm diameter on the output side were drilled through steel foils of approximately 5-$\mu$m-thickness. Thus, depressions and apertures having diameters on the order of 0.5 $\mu$m and areas on the order of 0.25 $\mu m^2$ may be formed using laser radiation.

Mask-based techniques include those in which the masking material contacts the material to be machined, for example, masks formed using known lithographic techniques, and those in which the masking material does not contact the material to be machined, but which is provided between a directed source of excavating energy and the material to be machined (e.g., opaque masks having apertures formed therein, as well as semi-transparent masks such as gray-scale masks which provide variable beam intensity and thus variable machining rates). Material is removed in regions not protected such by such masks using any of a range of processes including physical processes (e.g., thermal sublimation and/or vaporization of the material that is removed), chemical processes (e.g., chemical breakdown and/or reaction of the material that is removed), or a combination of both. Specific examples of removal processes include wet and dry (plasma) etching techniques, and ablation techniques based on directed energetic beams. In a specific example of a technique combining these methods, a laser may be used to drill the majority of the way through a first material (e.g., a substrate material, or a nanoporous material or precursor), followed by an anisotropic etching process under conditions in which the etch rate of the first material far exceeds that of the underlying material (e.g., a porous reservoir material), resulting in a dramatic slowing of the etching process once the underlying material is reached.

It is noted that there is a great amount of available know-how in the semiconductor industry for etching apertures and depressions within a wide variety of materials.

Once a device is created that includes a substrate, one or more porous reservoirs, one or more nanoporous layers, and one or more apertures (which may be formed within the substrate, within the nanoporous layer, or both), then the porous reservoir(s) may be filled with a composition that contains at least one therapeutic agent. For example, at least one therapeutic agent in liquid form or a fluid (e.g., a solution or melt) containing at least one dissolved or dispersed therapeutic agent may be introduced into the apertures by any of a number of processes including, for example, dipping, spraying, extrusion, coating with an applicator (e.g., by roller or brush), spin-coating, web coating, techniques involving coating via mechanical suspension including air suspension, ink jet techniques, or filling via pipette(s) or other nozzle(s) (much like filling a tank), among others. Water, organic solvents, low-melting point materials, subcritical fluids, critical point fluids, supercritical fluids, and so forth can be used as carriers for the therapeutic agent(s). Further information on supercritical solvent loading may be found in Pub. No. US 2006/0127442 to Helmus et al. As noted above, the amount of therapeutic agent loaded will depend upon the volume and number of the porous reservoir(s) within the device. The amount of therapeutic agent loaded will also depend upon the concentration of therapeutic agent within the therapeutic-agent-containing fluid that is used to fill the porous reservoirs (assuming that a carrier or diluent is used). Thus, a range of therapeutic agent loading levels can be achieved. The amount of loading may be determined by those of ordinary skill in the art and will ultimately depend, for example, upon the disease or condition being treated, the age, sex and health of the subject, the nature of the therapeutic agent, and so forth.

Once the therapeutic agent(s) has been loaded into the porous reservoir(s) via the aperture(s), the aperture(s) is (are) plugged.

In some embodiments, the aperture(s) may be plugged using adjacent material (e.g., adjacent substrate material, adjacent nanoporous layer material and/or adjacent porous reservoir material). A plug may be formed out of the surrounding nanoporous or substrate material, for example, by a local melting operation. For instance, one may focus a laser on an area that includes the aperture and some of the material surrounding the aperture, thereby melting some of the material and allowing it to flow into the aperture and plug it (which process would, of course, form a depression where the aperture once was). One may also focus a laser on the reservoir material at the bottom of the aperture to melt the material plug the aperture from the bottom up. One may also form a plug out of the surrounding nanoporous material by material deformation (e.g., using a laser shock peening process like that described above).

In other embodiments, the aperture(s) is (are) plugged using a separate a plug forming material. Plug forming materials may be formed from suitable organic or inorganic materials, for example, selected from suitable members of the organic or inorganic materials described hereinabove.

Plug forming processes include, for example, processes in which a solution or melt containing or consisting of a plug forming material is directed into the aperture, for example, by metering a solution or melt from a pipette or some other suitable orifice into the aperture(s). In other processes a powder corresponding to a plug forming material is directed into the aperture and compressed, or a pre-formed plug is inserted into the aperture. As noted above, the aperture(s) may be completely filled with a plug forming material, in some instances extending laterally onto the surface of the substrate or nanoporous layer, or only the exterior end of the aperture(s) may be occupied by the plug forming material, among other possibilities.

The thus-formed plug may remain in place in vivo (e.g., it may be dimensionally stable) or it may be removed in vivo (e.g., because it is formed from a biodisintegrable material, because it is formed from a material that swells and is ejected from the aperture in vivo, etc.). For an example of the latter material, see, e.g., M. C. Gohel et al., "Modulation of active pharmaceutical material release from a novel 'tablet in capsule system' containing an effervescent blend," *Journal of Controlled Release* 79 (2002) 157-164, which describes drug delivery from a hard gelatin capsules that contain a hydrogel plug (e.g., a hydroxypropylmethylcellulose or guar gum plug). The hydrogel plug swells in vivo and is eventually ejected from the capsule thereby releasing drug.

Removable plugs may be desirable, for example, in the case of a biodegradable substrate, because they allow biological fluids to access a greater surface area of the substrate. Removable plugs may also be desirable, for example, where the substrate is biostable and bioactive, as they may provide enhanced cell attachment and growth. Removable plugs may further be desirable, for example, in a double layer structure (see, e.g., upper plug 140 in FIG. 16, discussed below), as they allow one to empty the therapeutic agent from the top layer while allowing a continuous release from the bottom layer (assuming that the material forming the lower plug 140 in FIG. 16 is such that it remains in place).

Using the above and other processes and materials, medical devices may be loaded and plugged. For example, the devices of FIGS. 2B and 3-8 are shown in FIGS. 10 and 11-16, respectively, after further processing. In these Figs., each of the porous reservoirs 120, 120*a* and 120*b* have been loaded with one or more therapeutic agents. The resulting therapeutic-agent-containing reservoirs 120*t*, 120*ta* and 120*tb* are then sealed with a plug 140.

Where multiple therapeutic agents are provided in a single porous reservoir, those therapeutic agents with larger hydrated radii may be released at slower rates than those having small hydrated radii. For example, an anti-inflammatory agent may be more quickly released then an anti-thrombotic agent having a larger hydrated radius.

In those embodiments having two or more independently accessible reservoirs (e.g., FIGS. 12, 13 and 16) the therapeutic-agent-containing reservoirs 120*ta* and 120*tb* may contain the same therapeutic agent or they may contain different therapeutic agents.

Figure 12:
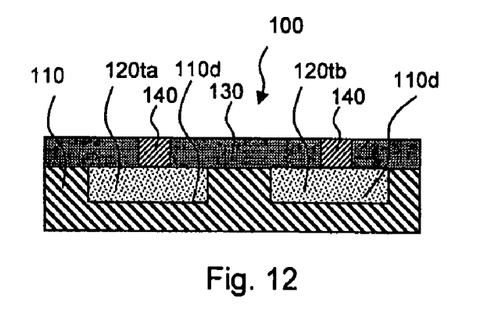
Figure 13:
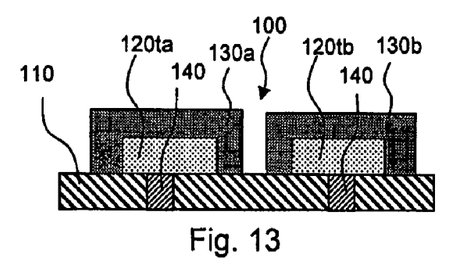
Figure 15:
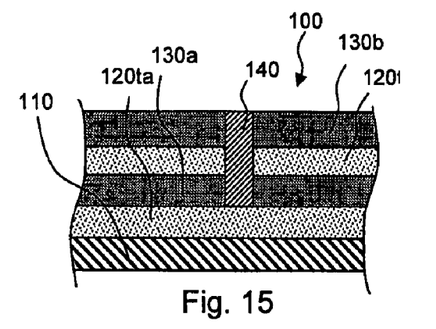

In FIGS. 12 and 13, for example, two differing therapeutic agents can be released from different therapeutic-agent-containing reservoirs 120*ta*, 120*tb* at different locations on the device surface. Moreover, in FIG. 13, nanoporous regions 130*a*, 130*b* may be provided with differing pore sizes to provide further control over therapeutic agent release. One example of a device in which it may be desirable to release differing therapeutic agents at different surface locations is a stent in which one or more first porous reservoirs filled with a first therapeutic agent (e.g., an antithrombotic agent) are present at the inner, luminal surface of the device, and one or more second porous reservoirs filled with a second therapeutic agent that differs from the first therapeutic agent (e.g., an antiproliferative agent) are present at the outer, abluminal surface.

One could also provide more than one therapeutic agent in separate porous reservoirs on the luminal surface of the stent or the abluminal surface of the stent.

For example, in a device like that of FIG. 12 or 13, anti-inflammatory agents could be quickly released through nanoporous layers having larger pore size (relative to the hydrated radius of the agent), whereas anti-thrombotic agents could be more slowly released through nanoporous layers having smaller pore size.

In FIG. 16, for example, a first therapeutic agent may be placed in the upper therapeutic-agent-containing reservoir 120*tb* and a second therapeutic agent may be placed in the lower therapeutic-agent-containing reservoir 120*ta*. In this case, the first agent has to pass through only the upper nanoporous layer 130*b* for release, whereas the second therapeutic agent has to pass through both the lower and upper nanoporous layers 130*a*, 130*b*. Assuming that the nanoporous layers 130*a*, 130*b* have the same characteristics and that the hydrated radius of the first therapeutic agent is less than or equal to the hydrated radius of the second therapeutic agent, the first therapeutic agent will experience less resistance to transport than the second therapeutic agent. On the other hand, the pores of the lower nanoporous layer 130*a* may be made smaller than the pores of the upper nanoporous layer 130*b*. This may be used, for example, to release the first agent more quickly than the second (e.g., where the first and second agents have approximately the same hydrated radius) or it may be used to create non-Fickian release for both therapeutic agents as previously discussed (e.g., where the second therapeutic agent has a smaller hydrated radius than the first therapeutic agent).

"Biologically active agents," "drugs," "therapeutic agents," "pharmaceutically active agents," "pharmaceutically active materials," and other related terms may be used interchangeably herein and include genetic therapeutic agents, non-genetic therapeutic agents and cells. A wide variety of therapeutic agents can be employed in conjunction with the present invention including those used for the treatment of a wide variety of diseases and conditions (i.e., the prevention of a disease or condition, the reduction or elimination of symptoms associated with a disease or condition, or the substantial or complete elimination of a disease or condition). Numerous therapeutic agents are described here.

Suitable non-genetic therapeutic agents for use in connection with the present invention may be selected, for example, from one or more of the following: (a) anti-thrombotic agents such as heparin, heparin derivatives, urokinase, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, antimicrobial peptides such as magainins, aminoglycosides and nitrofurantoin; (m) cytotoxic agents, cytostatic agents and cell proliferation affectors; (n) vasodilating agents; (o) agents that interfere with endogenous vasoactive mechanisms, (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) beta-blockers, (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, AII, AIII, AIV, AV, etc.).

Preferred non-genetic therapeutic agents include paclitaxel (including particulate forms thereof, for instance, protein-bound paclitaxel particles such as albumin-bound paclitaxel nanoparticles, e.g., ABRAXANE), sirolimus, everolimus, tacrolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well a derivatives of the forgoing, among others.

Exemplary genetic therapeutic agents for use in connection with the present invention include anti-sense DNA and RNA as well as DNA coding for: (a) anti-sense RNA, (b) tRNA or rRNA to replace defective or deficient endogenous molecules, (c) angiogenic factors including growth factors such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP1017 (SUPRATEK), lipids such as cationic lipids, liposomes, lipoplexes, nanoparticles, or microparticles, with and without targeting sequences such as the protein transduction domain (PTD).

Cells for use in connection with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and suitable examples may be selected from one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losarfin, (i) platelet adhesion inhibitors such as albumin and polyethylene oxide, 6) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (O) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin, cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Numerous additional therapeutic agents useful for the practice of the present invention are also disclosed in U.S. Pat. No. 5,733,925 to NeoRx Corporation.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A medical device comprising a substrate, a porous reservoir containing a therapeutic agent disposed over the substrate, a nanoporous layer disposed over the porous reservoir, and a plugged aperture located within the substrate or the nanoporous layer, wherein said medical device releases said therapeutic agent in vivo, wherein said plugged aperture is located within the nanoporous layer.

2. The medical device of claim 1, comprising a plurality of plugged apertures.

3. The medical device of claim 2, wherein at least one plugged aperture is located within the substrate and at least one plugged aperture is located within the nanoporous layer.

4. The medical device of claim 3, wherein the material forming the plug in the plugged aperture within the substrate covers the substrate surface.

5. The medical device of claim 1, further comprising an additional porous reservoir disposed over the nanoporous layer and an additional nanoporous layer disposed over the additional porous reservoir.

6. The medical device of claim 5, comprising a plugged aperture in the substrate and a plugged aperture in the additional nanoporous layer.

7. The medical device of claim 1, wherein width of the plug in the plugged aperture ranges from 1 to 4 times the width of the aperture at the outer surface of the aperture.

8. The medical device of claim 1, wherein the plug in the plugged aperture is biostable.

9. The medical device of claim 1, wherein the plug in the plugged aperture is biodisintegrable.

10. The medical device of claim 1, wherein the plug in the plugged aperture comprises a biostable polymer.

11. The medical device of claim 1, wherein the plug in the plugged aperture comprises a biodegradable polymer.

12. The medical device of claim 1, wherein the plug in the plugged aperture comprises a water-swellable polymer.

13. The medical device of claim 1, wherein the plug in the plugged aperture is formed from the nanoporous layer material.

14. The medical device of claim 1, wherein an additional plugged aperture is located within the substrate and wherein the plug in the plugged aperture is formed from the substrate material.

15. The medical device of claim 1, wherein said porous reservoir is at least partially disposed in a depression in said substrate.

16. The medical device of claim 1, comprising a plurality of porous reservoirs.

17. The medical device of claim 1, comprising a plurality of porous reservoirs covered by a single nanoporous layer.

18. The medical device of claim 1, comprising a plurality of porous reservoirs each covered by a different of nanoporous layer.

19. The medical device of claim 1, comprising a plurality of nanoporous layers.

20. The medical device of claim 1, comprising a plurality of nanoporous layers that differ in pore size or differ in thickness.

21. The medical device of claim 1, wherein the nanoporous layer is biostable.

22. The medical device of claim 1, wherein the nanoporous layer is biodegradable.

23. The medical device of claim 1, wherein the nanoporous layer is polymeric.

24. The medical device of claim 1, wherein the nanoporous layer is metallic.

25. The medical device of claim 1, wherein the nanoporous layer is ceramic.

26. The medical device of claim 1, wherein the nanoporous layer is a polymeric-ceramic hybrid.

27. The medical device of claim 1, wherein the nanoporous layer comprises a parallel pore structure.

28. The medical device of claim 1, wherein the nanoporous layer comprises an interconnected pore structure.

29. The medical device of claim 1, wherein the pore size of the nanoporous layer on the side adjacent to the porous reservoir is greater than the pore size on the opposite side.

30. The medical device of claim 1, wherein the substrate material is biostable.

31. The medical device of claim 1, wherein the substrate material is biodisintegrable.

32. The medical device of claim 1, wherein the substrate material is metallic.

33. The medical device of claim 1, wherein the substrate is a polymeric-ceramic hybrid.

34. The medical device of claim 1, selected from a stent and an aneurism treatment device.

35. The medical device of claim 1, wherein said medical device is adapted for implantation or insertion into the vasculature, urogenital system, digestive system, or biliary tract.

36. The medical device of claim 1, comprising a plurality of different therapeutic agents.

37. The medical device of claim 1, wherein the release is zero-order release.

38. The medical device of claim 1, wherein said therapeutic agent is selected from one or more of the group consisting of anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, TGF-β elevating agents, and agents that interfere with endogenous vasoactive mechanisms.

39. A method of forming the medical device of claim 1 comprising, (a) forming the porous reservoir over the substrate, (b) forming the nanoporous layer over the porous reservoir, (c) forming the aperture within the substrate or the nanoporous layer, (d) filling the porous reservoir with the therapeutic agent through the aperture, and (d) plugging said aperture.

* * * * *

UNITED STATES PATENT AND TRADEMARK OFFICE
CERTIFICATE OF CORRECTION

| | |
|---|---|
| PATENT NO. | : 8,187,255 B2 |
| APPLICATION NO. | : 11/701768 |
| DATED | : May 29, 2012 |
| INVENTOR(S) | : Jan Weber and Liliana Atanasoska |

Page 1 of 1

It is certified that error appears in the above-identified patent and that said Letters Patent is hereby corrected as shown below:

Col. 11, line 32, after "as" change "discuss" to --discussed--.

Col. 13, line 61-62, after "it" change "though" to --through--.

Col. 15, line 15, after "so" change "may then" to --they may--.

Signed and Sealed this
Seventh Day of August, 2012

David J. Kappos
*Director of the United States Patent and Trademark Office*